United States Patent
Miura et al.

[11] Patent Number: 5,869,664
[45] Date of Patent: Feb. 9, 1999

[54] PROCESS FOR PREPARING ADDUCT OF IMIDAZOLE-ISOCYANURIC ACID

[75] Inventors: Mareki Miura; Yoshinobu Ohnuma, both of Yokkaichi, Japan

[73] Assignee: Shell Oil Company, Houston, Tex.

[21] Appl. No.: 903,703

[22] Filed: Jul. 31, 1997

[30] Foreign Application Priority Data

Jul. 31, 1996 [JP] Japan ................................. 8-201637

[51] Int. Cl.⁶ ........................ C07D 403/04; C07D 403/14
[52] U.S. Cl. ............................................. 544/222; 544/207
[58] Field of Search ................................ 544/222, 207

[56] References Cited

U.S. PATENT DOCUMENTS

| | | | |
|---|---|---|---|
| 4,189,577 | 2/1980 | Sawa et al. | 544/222 |
| 4,205,156 | 5/1980 | Sawa et al. | 528/117 |

FOREIGN PATENT DOCUMENTS 53-116391  10/1978  Japan .
6 1235-426-A  10/1986  Japan .

*Primary Examiner*—John M. Ford

[57] ABSTRACT

A process for preparing an adduct of imidazole-isocyanuric acid which comprises an addition reaction in which a homogeneous aqueous solution of an imidazole compound represented by general formula (I) described below;

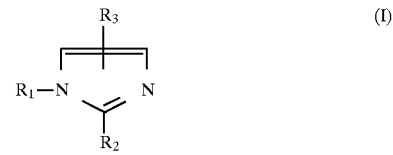

wherein $R_1$ represents a hydrogen atom, β-cyanoethyl group, benzyl group, or β-{3,5-diamino-S-triazinyl-(1)}-ethyl group, $R_2$ represents an alkyl group having a carbon number of 1 to 20 or a phenyl group, $R_3$ represents a hydrogen atom or a methyl group is added to a homogeneous aqueous solution of isocyanuric acid which is heated to at least 70° C.

6 Claims, No Drawings

PROCESS FOR PREPARING ADDUCT OF IMIDAZOLE-ISOCYANURIC ACID

FIELD OF THE INVENTION

The present invention relates to a process for preparing an adduct of imidazole-isocyanuric acid which is useful as a curing agent for epoxy resins and an accelerator thereof.

BACKGROUND OF THE INVENTION

Heretofore, in a process for obtaining an adduct of imidazole-isocyanuric acid, water, aqueous solution of acetic acid, or dimethylformamide is used as a solvent. An imidazole compound and isocyanuric acid are charged into the solvent as it is in a solid to react by addition, and then crystallized while cooling, thereby being obtained an adduct of imidazole-isocyanuric acid. (confer JP-A-53-116391).

However, the conventional process has been problematic, since the adduct of imidazole-isocyanuric acid produced is remarkably poor in solubility in the solvents, whereby the adduct of imidazole-isocyanuric acid crystallizes before starting materials are dissolved, and the starting materials are taken into the adduct, resulting in that there is required a troublesome operation such as recrystallization, etc. in order to obtain a product having high purity. Further, to obtain a product having high purity by one operational step, it has been prepared by a process in which a reaction is carried out in a homogeneous system by employing a large amount of solvents, and then product is crystallized. However, the process cannot provide a large amount of the product, resulting in that efficiency of a reactor is very low. Still further, since reaction yield is also low, there is a problem in view of being economically disadvantageous.

In addition, there is described a process in which a polyepoxy resin is directly mixed with an imidazole compound and isocyanuric acid with a roll (confer JP-A-61-235426). However, the process includes a problem that isocyanuric acid does not readily react by addition to an imidazole compound because isocyanuric acid does not sufficiently dissolve into the epoxy resin, resulting in that the adduct of imidazole-isocyanuric acid cannot exhibit inherent functions as a curing agent.

SUMMARY OF THE INVENTION

The present invention provides an economically advantageous process for preparing an adduct of imidazole-isocyanuric acid by which the above-described problems are solved, and a large amount of the adduct can be readily prepared with excellent reaction yield, resulting in that efficiency of a reactor is largely improved.

A process for preparing an adduct of imidazole-isocyanuric acid of the present invention is provided comprising reacting a homogeneous aqueous solution of an imidazole compound represented by general formula (I) described below;

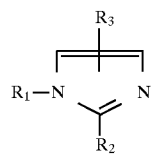

(I)

wherein $R_1$ is a hydrogen atom, $\beta$-cyanoethyl group, benzyl group, or $\beta$-{3,5-diamino-S-triazinyl-(1)}-ethyl group, $R_2$ is an alkyl group having a carbon number of 1 to 20 or a phenyl group, $R_3$ is a hydrogen atom or a methyl group and a homogeneous aqueous solution of isocyanuric acid which is heated to a temperature of at least 70° C.

DETAILED DESCRIPTION OF THE INVENTION

The imidazole compound represented by general formula (I) which can be employed in the present invention, there are exemplified 2-methylimidazole, 2-phenylimidazole, 1-($\beta$-cyanoethyl)-2-phenylimidazole, 1-benzyl-2-methylimidazole, 2,4-diamino-6-[2'-methylimidazolyl-(1')]ethyl-S-triazine, 2,4-diamino-6-[2'-undecylimidazolyl-(1')]ethyl-S-triazine, and 2,4-diamino-6-[2'-ethyl-4'(5')-methylimidazolyl-(1')]ethyl-S-triazine, etc.

The process for preparing an adduct of imidazole-isocyanuric acid according to the present invention is characterized in that there are individually prepared two aqueous solutions a solvent into which imidazole compound and isocyanuric acid are completely dissolved, respectively.

The aqueous solution of isocyanuric acid is heated to a temperature of not less than 70° C., preferably from 70° to 100° C., and isocyanuric acid must be maintained in a completely dissolving state.

In the case where the temperature of the aqueous solution of isocyanuric acid is less than 70° C., solubility of isocyanuric acid becomes remarkably poor, unpreferably resulting in that it crystallizes. The concentration of isocyanuric acid preferably is in a range of from 1 to 10% by weight.

In the case where the concentration of isocyanuric acid is less than 1% by weight, a yield of the adduct of imidazole-isocyanuric acid obtained unpreferably becomes worse. Further, in the case where it exceeds 10% by weight, there are required temperatures exceeding 100° C. and relatively high pressure in order to obtain a homogeneous aqueous solution of isocyanuric acid, unpreferably resulting in that there become required particular reaction equipment.

The aqueous solution of imidazole is heated to temperatures in a range of from 0° to 100° C., preferably from 50° to 100° C., and imidazole compound be maintained in a completely dissolving state. The concentration of imidazole compound preferably is in a range of from 5 to 50% by weight. In the case where it is less than 5% by weight, there unpreferably becomes worse a yield of a product.

Further, in the case where it exceeds 50% by weight, there becomes excessively high the concentration of the adduct of imidazole-isocyanuric acid in reaction system, and operations such as agitation become difficult, unpreferably resulting in that there cannot be obtained the adduct of imidazole-isocyanuric acid having a high purity.

The addition reaction is carried out in a range of from 0.95 to 1.05 mol of the imidazole compound based on 1 mol of isocyanuric acid. In the addition reaction, the aqueous solution of the imidazole dissolved according to the above-described conditions is added dropwise into the aqueous solution of isocyanuric acid dissolved according to the above-described conditions at a temperature in the reaction system of not less than 70° C., preferably while maintaining at 70° to 100° C. over 0.5 to 3 hours. In the reaction, although the aqueous solution of the imidazole is preferably added dropwise into the aqueous solution of isocyanuric acid, the aqueous solution of isocyanuric acid may be added dropwise into the aqueous solution of the imidazole.

After the dropwise addition, a reaction for aging is carried out at the temperature not less than 70° C., preferably while maintaining at a temperature of from 70° to 100° C. for 0.5 to 3 hours, followed by cooling to 50° C. and separating by filtration of a crystalline adduct of imidazole-isocyanuric acid crystallized. The crystalline adduct is dried at a temperature ranging from 50° to 130° C. for 1 to 50 hours to obtain a desired adduct of imidazole-isocyanuric acid.

EXAMPLES

In the following, the present invention is described in more detail by referring to Examples, Comparative Examples, Application Examples, and Comparative Application Examples.

Example 1

A 1-liter four-necked flask equipped with a thermometer, an agitator, a condenser, and a dropwise funnel was charged with 12.9 g (0.1 mol) of isocyanuric acid and 430 g of pure water, followed by agitating at the temperature of 95° C. to obtain a homogeneous aqueous solution of isocyanuric acid and maintaining temperature in the flask at 95° C. (the concentration of isocyanuric acid: 2.9% by weight).

A 500-ml flask was charged with 21.9 g (0.1 mol) of 2,4-diamino-6-[2'-methylimidazolyl-(1')]ethyl-S-triazine and 219 g of pure water, followed by agitating at the temperature of 95° C. to obtain a homogeneously dissolved aqueous solution of imidazole (the concentration of imidazole: 9.1% by weight). Subsequently, the solution was transferred to a dropwise funnel equipped with a unit for keeping warmth to maintain the internal temperature at 95° C.

Subsequently, the aqueous solution of imidazole was added dropwise into the aqueous solution of isocyanuric acid maintained at 95° C. over 1 hour. After the completion of dropwise addition, addition reaction was further carried out at 95° C. for 1 hour.

After the completion of the reaction, a reaction solution was cooled to 40° C. After a crystallized product was separated by filtration, it was dried at 80° C. for 24 hours to obtain 36.9 g of a white powdered adduct of imidazole-isocyanuric acid (yield: 96.1%). IR analysis and mass-spectrum analysis relating to the adduct were carried out to identify a desired product. Furthermore, an amine value of the adduct was 288.

Comparative Example 1

A 1-liter four-necked flask equipped with an agitator, a thermometer, and a condenser was charged with 12.9 g (0.1 mol) of isocyanuric acid and 21.9 g (0.1 mol) of 2,4-diamino-6-[2'-methylimidazolyl-(1')]ethyl-S-triazine, and 649 g of pure water, followed by raising temperature to 100° C. while agitating. In reaction system, a reaction proceeded in a heterogeneous state because starting materials were not dissolved, and the reaction system started to change to a gruel-state at the vicinity of 80° C., whereby it is guessed that there crystallized an adduct of imidazole-isocyanuric acid. After the temperature in the reaction system attained to 100° C., agitation was further continued in the heterogeneous state for 1 hour.

After the completion of the reaction, a reaction solution was cooled to 40° C. After a gruel-state content was separated by filtration, a cake obtained was recrystallized with 2.5 liters of pure water, and crystal was dried at 80° C. for 24 hours to obtain 23.2 g of a white powdered adduct of imidazole-isocyanuric acid (yield: 60.4%). An amine value of the adduct was 286.

Comparative Example 2

A 5-liter four-necked flask equipped with an agitator, a thermometer, and a condenser was charged with 12.9 g (0.1 mol) of isocyanuric acid and 21.9 g (0.1 mol) of 2,4-diamino-6-[2'-methylimidazolyl-(1')]ethyl-S-triazine, and 3500 g of pure water, followed by raising temperature to 100° C. while agitating. After reaction system changed to a homogeneous state, addition reaction was further continued while agitating at 100° C. for 1 hour.

After the completion of the reaction, a reaction solution was cooled to 40° C. to prepare crystal. After separated by filtration, the crystal was dried at 80° C. for 24 hours to obtain 27.6 g of a white powdered adduct of imidazole-isocyanuric acid (yield: 71.9%). An amine value of the adduct was 289.

Example 2

A 1-liter four-necked flask equipped with a thermometer, an agitator, a condenser, and a dropwise funnel was charged with 12.9 g (0.1 mol) of isocyanuric acid and 430 g of pure water, followed by agitating at the temperature of 95° C. to obtain a homogeneous aqueous solution of isocyanuric acid and maintaining temperature in the flask at 95° C. (the concentration of isocyanuric acid: 2.9% by weight).

Separately, 8.2 g (0.1 mol) of 2-methylimidazole was homogeneously dissolved into 30 g of pure water at the temperature of 50° C. to prepare an aqueous solution of imidazole (the concentration of imidazole: 21.5% by weight). The solution was transferred to a dropwise funnel, and internal temperature was maintained at 50° C.

The successive operations were identically followed as in the Example 1 to obtain 20.1 g of a white powdered adduct of imidazole-isocyanuric acid (yield: 95.3%). IR analysis and mass-spectrum analysis relating to the adduct were carried out to identify a desired product. Furthermore, an amine value of the adduct was 530.

Example 3

A 1-liter four-necked flask equipped with a thermometer, an agitator, a condenser, and a dropwise funnel was charged with 12.9 g (0.1 mol) of isocyanuric acid and 430 g of pure water, followed by agitating at the temperature of 95° C. to obtain a homogeneous aqueous solution of isocyanuric acid and maintaining temperature in the flask at 95° C. (the concentration of isocyanuric acid: 2.9% by weight).

Separately, 14.4 g (0.1 mol) of 2-phenylimidazole was homogeneously dissolved in 216 g of pure water at the temperature of 50° C. to prepare an aqueous solution of imidazole (the concentration of imidazole: 6.25% by weight). The solution was transferred to a dropwise funnel, and internal temperature was maintained at 95° C.

The successive operations were identically followed as in the Example 1 to obtain 26.5 g of a white powdered adduct of imidazole-isocyanuric acid (yield: 97.1%). IR analysis and mass-spectrum analysis relating to the adduct were carried out to identify a desired product. Furthermore, an amine value of the adduct was 408.

Application Example 1

There were mixed 5 g of the adduct of imidazole-isocyanuric acid obtained in the Example 1, 100 g of Epikote 828 (manufactured by Yuka Shell Epoxy, K.K.) as an epoxy resin, and 2 g of Aerosyl #300 (manufactured by Nihon Aerosyl, Ltd.) as an agent for preventing precipitation in an automatic mortar for 2 hours. There are shown properties of a mixture obtained in Table 1.

Comparative Application Example 1

The identical procedures were followed as in the Application Example 1 except that there was employed 5 g of the adduct of imidazole-isocyanuric acid obtained in the Comparative Example 1 to obtain a mixture. There are shown properties in Table 1.

Comparative Application Example 2

There were mixed 1.9 g of isocyanuric acid and 3.1 g of 2,4-diamino-6-[2'-methylimidazolyl-(1')]ethyl-S-triazine in place of the adduct of imidazole-isocyanuric acid, 100 g of Epikote 828 (manufactured by Yuka Shell Epoxy, K.K.) as an epoxy resin, and 2 g of Aerosyl #300 (manufactured by Nihon Aerosyl, Ltd.) as an agent for preventing precipitation in an automatic mortar for 2 hours. There are shown properties of a mixture obtained in Table 1.

TABLE

| | | Application Example 1 | Comparative Application Example 1 | Comparative Application Example 2 |
|---|---|---|---|---|
| Stability in storage (25° C.)*1 | | >6 months | >6 months | 1 month |
| Gelation time (second) | 120° C. | 580 | 595 | 700 |
| | 150° C. | 111 | 115 | 150 |
| | 180° C. | 41 | 41 | 45 |
| Heat distortion temperature (°C.)*2 | | 146 | 145 | 110 |

*1: Volume of 100 g, time of period attaining to twofold of initial viscosity
*2: 100° C. 2 hours + 150° C. 4 hours (curing condition)

According to the process of the present invention, there can be readily prepared an adduct of imidazole-isocyanuric acid with a high yield, and also the amount of a product obtained increases, resulting in being an economically excellent process.

Further, the adduct of imidazole-isocyanuric acid obtained can be employed as a curing agent for epoxy resins, and is widely used for powdered electric insulator, adhesives, and materials for molding.

We claim:

1. A process for preparing an adduct of imidazole-isocyanuric acid comprising reacting a homogeneous aqueous solution of an imidazole compound represented by general formula (I)

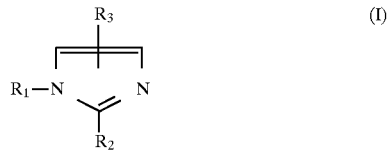

wherein $R_1$ is a hydrogen atom, β-cyanoethyl group, benzyl group, or β-{3,5-diamino-S-triazinyl-(1)}-ethyl group, $R_2$ is an alkyl group having a carbon number of 1 to 20 or a phenyl group, $R_3$ is a hydrogen atom or a methyl group and a homogeneous aqueous solution of isocyanuric acid heated to a temperature of at least 70° C.

2. The process of claim 1 wherein said aqueous solution of isocyanuric acid is heated at a temperature of from 70° to 100° C.

3. The process of claim 1 wherein the concentration of isocyanuric acid in said aqueous solution of isocyanuric acid is in a range of from 1 to 10% by weight.

4. The process of claim 1 wherein the concentration of said imidazole compound in said homogeneous aqueous solution containing an imidazole compound is in a range of from 5 to 50% by weight.

5. The process of claim 1 wherein said homogeneous aqueous solution of an imidazole compound is heated at a temperature of from 50° to 100° C.

6. The process of claim 1 wherein said imidazole compound is present in an amount from 0.95 to 1.05 mol based on 1 mol of isocyanuric acid.

* * * * *